United States Patent [19]
Stice et al.

[11] Patent Number: 5,945,577
[45] Date of Patent: Aug. 31, 1999

[54] CLONING USING DONOR NUCLEI FROM PROLIFERATING SOMATIC CELLS

[75] Inventors: Steven L. Stice, Belchertown; Jose Cibelli, Amherst; James Robl; Paul Golueke, both of Belchertown; F. Abel Ponce de Leon, Amherst; D. Joseph Jerry, Shutesbury, all of Mass.

[73] Assignee: University of Massachusetts as represented by its Amherst Campus, Amherst, Mass.

[21] Appl. No.: 08/781,752

[22] Filed: Jan. 10, 1997

[51] Int. Cl.$^6$ ............... C12N 5/00; C12N 15/00; A01K 67/00
[52] U.S. Cl. ............... 800/24; 800/14; 800/15; 800/16; 800/17; 435/325
[58] Field of Search ............... 800/2, DIG. 1; 435/172.3, 325, 350, 351, 352, 363, 366

[56] References Cited

U.S. PATENT DOCUMENTS

| | | | |
|---|---|---|---|
| 4,994,384 | 2/1991 | Prather et al. | 435/172.2 |
| 5,057,420 | 10/1991 | Massey | 435/172.2 |

FOREIGN PATENT DOCUMENTS

| | | |
|---|---|---|
| WO 95/16770 | 6/1995 | WIPO . |
| WO 95/17500 | 6/1995 | WIPO . |
| WO 95/34696 | 12/1995 | WIPO . |
| WO 96/07732 | 3/1996 | WIPO . |
| WO 97/07668 | 3/1997 | WIPO . |
| WO 97/07669 | 3/1997 | WIPO . |
| WO 97/37009 | 10/1997 | WIPO . |

OTHER PUBLICATIONS

Theriogenology, vol. 45, No. 1, p. 287, XP000605648.
Journal of Reproduction and Fertility Supplement, vol. 5, Jan. 1995, p. 60, XP000607293.
Molecular Reproduction and Development, vol. 38, No. 3, Jul. 1994, pp. 264–267, XP002067033.
Theriogenology, vol. 47, No. 1, p. 241, XP002067034.
Nature, vol. 385, No. 6619, pp. 810–813, XP002067035.
Science, vol. 278, No. 5346, pp. 2130–2133, XP002067036.
Biology of Reproduction, vol. 57, No. 2, pp. 385–393, XP002067037.
Journal of Neurochemistry, vol. 70, No. suppl. 1, p. S46, XP002067038.
Theriogenology, vol. 49, No. 1, pp. 129–138, XP002067444.
Sims et al. (1993) Proc. Natl. Acad. Sci. 90, 6143–6147.
Kono et al (1995) Expt. Cell Res. 221, 478–485.
Lovell–Badge et al Cold Spring Harbor Symp. Quant. Biol. (1985), 50 (Mol. Biol. Devel.), Cold Spring Harbor Lab. Press, Cold Spring Harbor, NY, pp. 707–711.
Wilmut et al (1997) Nature 385, 810–813.
Campbell et al (1996) Nature 380, 64–66.
Schultz et al (1995) Sem. Cell Biol. 6, 201–208.
Hyttinen et al (1994) Bioltechnology 12, 606–608.

*Primary Examiner*—Deborah Crouch
*Attorney, Agent, or Firm*—Burns, Doane, Swecker & Mathis, LLP

[57] ABSTRACT

An improved method of nuclear transfer involving the transplantation of donor differentiated cell nuclei into enucleated oocytes of the same species as the donor cell is provided. The resultant nuclear transfer units are useful for multiplication of genotypes and transgenic genotypes by the production of fetuses and offspring, and for production of isogenic CICM cells, including human isogenic embryonic or stem cells. Production of genetically engineered or transgenic mammalian embryos, fetuses and offspring is facilitated by the present method since the differentiated cell source of the donor nuclei can be genetically modified and clonally propagated.

24 Claims, No Drawings

CLONING USING DONOR NUCLEI FROM PROLIFERATING SOMATIC CELLS

FIELD OF THE INVENTION

The present invention relates to cloning procedures in which cell nuclei derived from differentiated fetal or adult, mammalian cells are transplanted into enucleated mammalian oocytes of the same species as the donor nuclei. The nuclei are reprogrammed to direct the development of cloned embryos, which can then be transferred into recipient females to produce fetuses and offspring, or used to produce cultured inner cell mass cells (CICM). The cloned embryos can also be combined with fertilized embryos to produce chimeric embryos, fetuses and/or offspring.

BACKGROUND OF THE INVENTION

Methods for deriving embryonic stem (ES) cell lines in vitro from early preimplantation mouse embryos are well known. (See, e.g., Evans et al., *Nature*, 29:154–156 (1981); Martin, *Proc. Natl. Acad. Sci., USA*, 78:7634–7638 (1981)). ES cells can be passaged in an undifferentiated state, provided that a feeder layer of fibroblast cells (Evans et al., Id.) or a differentiation inhibiting source (Smith et al., *Dev. Biol.*, 121:1–9 (1987)) is present.

ES cells have been previously reported to possess numerous applications. For example, it has been reported that ES cells can be used as an in vitro model for differentiation, especially for the study of genes which are involved in the regulation of early development. Mouse ES cells can give rise to germline chimeras when introduced into preimplantation mouse embryos, thus demonstrating their pluripotency (Bradley et al., *Nature*, 309:255–256 (1984)).

In view of their ability to transfer their genome to the next generation, ES cells have potential utility for germline manipulation of livestock animals by using ES cells with or without a desired genetic modification. Moreover, in the case of livestock animals, e.g., ungulates, nuclei from like preimplantation livestock embryos support the development of enucleated oocytes to term (Smith et al., *Biol. Reprod.*, 40:1027–1035 (1989); and Keefer et al., *Biol. Reprod.*, 50:935–939 (1994)). This is in contrast to nuclei from mouse embryos which beyond the eight-cell stage after transfer reportedly do not support the development of enucleated oocytes (Cheong et al, *Biol. Reprod.*, 48:958 (1993)). Therefore, ES cells from livestock animals are highly desirable because they may provide a potential source of totipotent donor nuclei, genetically manipulated or otherwise, for nuclear transfer procedures.

Some research groups have reported the isolation of purportedly pluripotent embryonic cell lines. For example, Notarianni et al., *J. Reprod. Fert. Suppl.*, 43:255–260 (1991), reports the establishment of purportedly stable, pluripotent cell lines from pig and sheep blastocysts which exhibit some morphological and growth characteristics similar to that of cells in primary cultures of inner cell masses isolated immunosurgically from sheep blastocysts. Also, Notarianni et al., *J. Reprod. Fert. Suppl.* 41:51–56 (1990) discloses maintenance and differentiation in culture of putative pluripotential embryonic cell lines from pig blastocysts. Gerfen et al., *Anim. Biotech*, 6(1):1–14 (1995) discloses the isolation of embryonic cell lines from porcine blastocysts. These cells are stably maintained in mouse embryonic fibroblast feeder layers without the use of conditioned medium, and reportedly differentiate into several different cell types during culture.

Further, Saito et al., *Roux's Arch. Dev. Biol.*, 201:134–141 (1992) reports cultured, bovine embryonic stem cell-like cell lines which survived three passages, but were lost after the fourth passage. Handyside et al., *Roux's Arch. Dev. Biol.*, 196:185–190 (1987) discloses culturing of immunosurgically isolated inner cell masses of sheep embryos under conditions which allow for the isolation of mouse ES cell lines derived from mouse ICMs. Handyside et al. reports that under such conditions, the sheep ICMs attach, spread, and develop areas of both ES cell-like and endoderm-like cells, but that after prolonged culture only endoderm-like cells are evident.

Recently, Cherny et al., *Theriogenology*, 41:175 (1994) reported purportedly pluripotent bovine primordial germ cell-derived cell lines maintained in long-term culture. These cells, after approximately seven days in culture, produced ES-like colonies which stained positive for alkaline phosphatase (AP), exhibited the ability to form embryoid bodies, and spontaneously differentiated into at least two different cell types. These cells also reportedly expressed mRNA for the transcription factors OCT4, OCT6 and HES1, a pattern of homeobox genes which is believed to be expressed by ES cells exclusively.

Also recently, Campbell et al., *Nature*, 380:64–68 (1996) reported the production of live lambs following nuclear transfer of cultured embryonic disc (ED) cells from day nine ovine embryos cultured under conditions which promote the isolation of ES cell lines in the mouse. The authors concluded that ED cells from day nine ovine embryos are totipotent by nuclear transfer and that totipotency is maintained in culture.

Van Stekelenburg-Hamers et al., *Mol. Reprod. Dev.*, 40:444–454 (1995), reported the isolation and characterization of purportedly permanent cell lines from inner cell mass cells of bovine blastocysts. The authors isolated and cultured ICMs from 8 or 9 day bovine blastocysts under different conditions to determine which feeder cells and culture media are most efficient in supporting the attachment and outgrowth of bovine ICM cells. They concluded that the attachment and outgrowth of cultured ICM cells is enhanced by the use of STO (mouse fibroblast) feeder cells (instead of bovine uterus epithelial cells) and by the use of charcoal-stripped serum (rather than normal serum) to supplement the culture medium. Van Stekelenburg et al reported, however, that their cell lines resembled epithelial cells more than pluripotent ICM cells.

Smith et al., WO 94/24274, published Oct. 27, 1994, Evans et al, WO 90/03432, published Apr. 5, 1990, and Wheeler et al, WO 94/26889, published Nov. 24, 1994, report the isolation, selection and propagation of animal stem cells which purportedly may be used to obtain transgenic animals. Evans et al. also reported the derivation of purportedly pluripotent embryonic stem cells from porcine and bovine species which assertedly are useful for the production of transgenic animals. Further, Wheeler et al, WO 94/26884, published Nov. 24, 1994, disclosed embryonic stem cells which are assertedly useful for the manufacture of chimeric and transgenic ungulates.

Thus, based on the foregoing, it is evident that many groups have attempted to produce ES cell lines, e.g., because of their potential application in the production of cloned or transgenic embryos and in nuclear transplantation.

The use of ungulate inner cell mass (ICM) cells for nuclear transplantation has also been reported. For example, Collas et al., *Mol. Reprod. Dev.*, 38:264–267 (1994) discloses nuclear transplantation of bovine ICMs by microinjection of the lysed donor cells into enucleated mature oocytes. Collas et al. disclosed culturing of embryos in vitro for seven days to produce fifteen blastocysts which, upon transferral into bovine recipients, resulted in four pregnancies and two births. Also, Keefer et al., *Biol. Reprod.*, 50:935–939 (1994), disclosed the use of bovine ICM cells as donor nuclei in nuclear transfer procedures, to produce blastocysts which, upon transplantation into bovine recipients, resulted in several live offspring. Further, Sims et al., *Proc. Natl. Acad. Sci., USA*, 90:6143–6147 (1993), disclosed the production of calves by transfer of nuclei from short-term in vitro cultured bovine ICM cells into enucleated mature oocytes.

The production of live lambs following nuclear transfer of cultured embryonic disc cells has also been reported (Campbell et al., *Nature*, 380:64–68 (1996)). Still further, the use of bovine pluripotent embryonic cells in nuclear transfer and the production of chimeric fetuses has been reported (Stice et al., *Biol. Reprod.*, 54:100–110 (1996); Collas et al, *Mol. Reprod. Dev.*, 38:264–267 (1994)). Collas et al demonstrated that granulosa cells (adult cells) could be used in a bovine cloning procedure to produce embryos. However, there was no demonstration of development past early embryonic stages (blastocyst stage). Also, granulosa cells are not easily cultured and are only obtainable from females. Collas et al did not attempt to propagate the granulosa cells in culture or try to genetically modify those cells.

While multiplications of genotypes are possible using embryonic cells as donors, there are problems with current methods. For example, by current methods, embryo cloning can only be done using a limited number of embryonic donor nuclei (less than 100), or with in vitro cell lines. It is unknown whether the embryonic genome encodes a superior genotype until the cloned animal becomes an adult.

There also exist problems in the area of producing transgenic mammals. By current methods, heterologous DNA is introduced into either early embryos or embryonic cell lines that differentiate into various cell types in the fetus and eventually develop into a transgenic animal. However, many early embryos are required to produce one transgenic animal and, thus, this procedure is very inefficient. Also, there is no simple and efficient method of selecting for a transgenic embryo before going through the time and expense of putting the embryos into surrogate females. In addition, gene targeting techniques cannot be easily accomplished with early embryo transgenic procedures.

Embryonic stem cells in mice have enabled researchers to select for transgenic cells and perform gene targeting. This allows more genetic engineering than is possible with other transgenic techniques. However, embryonic stem cell lines and other embryonic cell lines must be maintained in an undifferentiated state that requires feeder layers and/or the addition of cytokines to media. Even if these precautions are followed, these cells often undergo spontaneous differentiation and cannot be used to produce transgenic offspring by currently available methods. Also, some embryonic cell lines have to be propagated in a way that is not conducive to gene targeting procedures.

Therefore, notwithstanding what has previously been reported in the literature, there exists a need for improved methods of cloning mammalian cells.

OBJECTS AND SUMMARY OF THE INVENTION

It is an object of the invention to provide novel and improved methods for producing cloned mammalian cells.

It is a more specific object of the invention to provide a novel method for cloning mammalian cells which involves transplantation of the nucleus of a differentiated mammalian cell into an enucleated oocyte of the same species.

It is another object of the invention to provide a method for multiplying adult mammals having proven genetic superiority or other desirable traits.

It is another object of the invention to provide an improved method for producing genetically engineered or transgenic mammals (i.e., embryos, fetuses, offspring).

It is a more specific object of the invention to provide a method for producing genetically engineered or transgenic mammals by which a desired gene is inserted, removed or modified in a differentiated mammalian cell or cell nucleus prior to use of that differentiated cell or cell nucleus for formation of a NT unit.

It is another object of the invention to provide genetically engineered or transgenic mammals (i.e., embryos, fetuses, offspring) obtained by transplantation of the nucleus of a differentiated cell into an enucleated oocyte of the same species as the differentiated cell.

It is another object of the invention to provide a novel method for producing mammalian CICM cells which involves transplantation of a nucleus of a differentiated cell into an enucleated oocyte of the same species as the differentiated cell.

It is another object of the invention to provide CICM cells produced by transplantation of the nucleus of a differentiated mammalian cell into an enucleated oocyte of the same species as the differentiated cell.

It is a more specific object of the invention to provide a method for producing human CICM cells which involves transplantation of nuclei of a human cell, e.g., a human adult cell, into an enucleated human oocyte.

It is another object of the invention to use such CICM cells for therapy or diagnosis.

It is a specific object of the invention to use such CICM cells, including human and ungulate CICM cells, for treatment or diagnosis of any disease wherein cell, tissue or organ transplantation is therapeutically or diagnostically beneficial. The CICM cells may be used within the same species or across species.

It is another object of the invention to use tissues derived from NT embryos, fetuses or offspring, including human and ungulate tissues, for treatment or diagnosis of any disease wherein cell, tissue or organ transplantation is therapeutically or diagnostically beneficial. The tissues may be used within the same species or across species.

It is another specific object of the invention to use the CICM cells produced according to the invention for the production of differentiated cells, tissues or organs.

It is a more specific object of the invention to use the human CICM cells produced according to the invention for the production of differentiated human cells, tissues or organs.

It is another specific object of the invention to use the CICM cells produced according to the invention in vitro, e.g. for study of cell differentiation and for assay purposes, e.g. for drug studies.

It is another object of the invention to provide improved methods of transplantation therapy, comprising the usage of isogenic or syngenic cells, tissues or organs produced from the CICM cells produced according to the invention. Such therapies include by way of example treatment of diseases and injuries including Parkinson's, Huntington's, Alzheimer's, ALS, spinal cord injuries, multiple sclerosis, muscular dystrophy, diabetes, liver diseases, heart disease, cartilage replacement, burns, vascular diseases, urinary tract diseases, as well as for the treatment of immune defects, bone marrow transplantation, cancer, among other diseases.

It is another object of the invention to provide genetically engineered or transgenic CICM cells produced by inserting, removing or modifying a desired gene in a differentiated mammalian cell or cell nucleus prior to use of that differentiated cell or cell nucleus for formation of a NT unit.

It is another object of the invention to use the transgenic or genetically engineered CICM cells produced according to the invention for gene therapy, in particular for the treatment and/or prevention of the diseases and injuries identified, supra.

It is another object of the invention to use the CICM cells produced according to the invention or transgenic or genetically engineered CICM cells produced according to the invention as nuclear donors for nuclear transplantation.

Thus, in one aspect, the present invention provides a method for cloning a mammal (e.g., embryos, fetuses, offspring). The method comprises:

(i) inserting a desired differentiated mammalian cell or cell nucleus into an enucleated mammalian oocyte of the same species as the differentiated cell or cell nucleus, under conditions suitable for the formation of a nuclear transfer (NT) unit;

(ii) activating the resultant nuclear transfer unit;

(iii) culturing said activated nuclear transfer unit until greater than the 2-cell developmental stage; and (iv) transferring said cultured NT unit to a host mammal such that the NT unit develops into a fetus.

The cells, tissues and/or organs of the fetus are advantageously used in the area of cell, tissue and/or organ transplantation.

The present invention also includes a method of cloning a genetically engineered or transgenic mammal, by which a desired gene is inserted, removed or modified in the differentiated mammalian cell or cell nucleus prior to insertion of the differentiated mammalian cell or cell nucleus into the enucleated oocyte.

Also provided by the present invention are mammals obtained according to the above method, and offspring of those mammals.

The present invention is preferably used for cloning ungulates.

In another aspect, the present invention provides a method for producing CICM cells. The method comprises:

(i) inserting a desired differentiated mammalian cell or cell nucleus into an enucleated mammalian oocyte of the same species as the differentiated cell or cell nucleus, under conditions suitable for the formation of a nuclear transfer (NT) unit;

(ii) activating the resultant nuclear transfer unit;

(iii) culturing said activated nuclear transfer unit until greater than the 2-cell developmental stage; and (iv) culturing cells obtained from said cultured NT unit to obtain CICM cells.

The CICM cells are advantageously used in the area of cell, tissue and organ transplantation.

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF THE INVENTION

The present invention provides improved procedures for cloning mammals by nuclear transfer or nuclear transplantation. In the subject application, nuclear transfer or nuclear transplantation or NT are used interchangeably.

According to the invention, cell nuclei derived from differentiated fetal or adult, mammalian cells are transplanted into enucleated mammalian oocytes of the same species as the donor nuclei. The nuclei are reprogrammed to direct the development of cloned embryos, which can then be transferred into recipient females to produce fetuses and offspring, or used to produce CICM cells. The cloned embryos can also be combined with fertilized embryos to produce chimeric embryos, fetuses and/or offspring.

Prior art methods have used embryonic cell types in cloning procedures. This includes work by Campbell et al (*Nature,* 380:64–68, 1996) and Stice et al (*Biol. Reprod.,* 54:100–110, 1996). In both of those studies, embryonic cell lines were derived from embryos of less than 10 days of gestation. In both studies, the cells were maintained on a feeder layer to prevent overt differentiation of the donor cell to be used in the cloning procedure. The present invention uses differentiated cells.

It was unexpected that cloned embryos with differentiated donor nuclei could develop to advanced embryonic and fetal stages. The scientific dogma has been that only embryonic or undifferentiated cell types could direct this type of development. It was unexpected that a large number of cloned embryos could be produced from these differentiated cell types. Also, the fact that new transgenic embryonic cell lines could be readily derived from transgenic cloned embryos was unexpected.

Thus, according to the present invention, multiplication of superior genotypes of mammals, including ungulates, is possible. This will allow the multiplication of adult animals with proven genetic superiority or other desirable traits. Progress will be accelerated, for example, in many important ungulate species. By the present invention, there are potentially billions of fetal or adult cells that can be harvested and used in the cloning procedure. This will potentially result in many identical offspring in a short period.

The present invention also allows simplification of transgenic procedures by working with a differentiated cell source that can be clonally propagated. This eliminates the need to maintain the cells in an undifferentiated state, thus, genetic modifications, both random integration and gene targeting, are more easily accomplished. Also by combining nuclear transfer with the ability to modify and select for these cells in vitro, this procedure is more efficient than previous transgenic embryo techniques. According to the present invention, these cells can be clonally propagated without cytokines, conditioned media and/or feeder layers, further simplifying and facilitating the transgenic procedure. When transfected cells are used in cloning procedures according to the invention, transgenic embryos are produced which can develop into fetuses and offspring. Also, these transgenic cloned embryos can be used to produce CICM cell lines or other embryonic cell lines. Therefore, the present invention eliminates the need to derive and maintain in vitro an undifferentiated cell line that is conducive to genetic engineering techniques.

The present invention can also be used to produce CICM cells, fetuses or offspring which can be used, for example, in cell, tissue and organ transplantation. By taking a fetal or adult cell from an animal and using it in the cloning procedure a variety of cells, tissues and possibly organs can be obtained from cloned fetuses as they develop through organogenesis. Cells, tissues, and organs can be isolated from cloned offspring as well. This process can provide a source of "materials" for many medical and veterinary therapies including cell and gene therapy. If the cells are transferred back into the animal in which the cells were derived, then immunological rejection is averted. Also, because many cell types can be isolated from these clones, other methodologies such as hematopoietic chimerism can be used to avoid immunological rejection among animals of the same species as well as between species.

Thus, in one aspect, the present invention provides a method for cloning a mammal. In general, the mammal will be produced by a nuclear transfer process comprising the following steps:

(i) obtaining desired differentiated mammalian cells to be used as a source of donor nuclei;

(ii) obtaining oocytes from a mammal of the same species as the cells which are the source of donor nuclei;

(iii) enucleating said oocytes;

(iv) transferring the desired differentiated cell or cell nucleus into the enucleated oocyte, e.g., by fusion or injection, to form NT units;

(v) activating the resultant NT unit;

(vi) culturing said activated nuclear transfer unit until greater than the 2-cell developmental stage; and (vii) transferring said cultured NT unit to a host mammal such that the NT unit develops into a fetus.

The present invention also includes a method of cloning a genetically engineered or transgenic mammal, by which a desired gene is inserted, removed or modified in the differentiated mammalian cell or cell nucleus prior to insertion of the differentiated mammalian cell or cell nucleus into the enucleated oocyte.

Also provided by the present invention are mammals obtained according to the above method, and offspring of those mammals. The present invention is preferably used for cloning ungulates.

The present invention further provides for the use of NT fetuses and NT and chimeric offspring in the area of cell, tissue and organ transplantation.

In another aspect, the present invention provides a method for producing CICM cells. The method comprises:

(i) inserting a desired differentiated mammalian cell or cell nucleus into an enucleated mammalian oocyte of the same species as the differentiated cell or cell nucleus, under conditions suitable for the formation of a nuclear transfer (NT) unit;

(ii) activating the resultant nuclear transfer unit;

(iii) culturing said activated nuclear transfer unit until greater than the 2-cell developmental stage; and (iv) culturing cells obtained from said cultured NT unit to obtain CICM cells.

The CICM cells are advantageously used in the area of cell, tissue and organ transplantation, or in the production of fetuses or offspring, including transgenic fetuses or offspring.

Preferably, the NT units will be cultured to a size of at least 2 to 400 cells, preferably 4 to 128 cells, and most preferably to a size of at least about 50 cells.

Nuclear transfer techniques or nuclear transplantation techniques are known in the literature and are described in many of the references cited in the Background of the Invention. See, in particular, Campbell et al, *Theriogenology*, 43:181 (1995); Collas et al, *Mol. Report Dev.*, 38:264–267 (1994); Keefer et al, *Biol. Reprod.*, 50:935–939 (1994); Sims et al, *Proc. Natl. Acad. Sci., USA*, 90:6143–6147 (1993); WO 94/26884; WO 94/24274, and WO 90/03432, which are incorporated by reference in their entirety herein. Also, U.S. Pat. Nos. 4,944,384 and 5,057,420 describe procedures for bovine nuclear transplantation.

Differentiated mammalian cells are those cells which are past the early embryonic stage. More particularly, the differentiated cells are those from at least past the embryonic disc stage (day 10 of bovine embryogenesis). The differentiated cells may be derived from ectoderm, mesoderm or endoderm.

Mammalian cells, including human cells, may be obtained by well known methods. Mammalian cells useful in the present invention include, by way of example, epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells, etc. Moreover, the mammalian cells used for nuclear transfer may be obtained from different organs, e.g., skin, lung, pancreas, liver, stomach, intestine, heart, reproductive organs, bladder, kidney, urethra and other urinary organs, etc. These are just examples of suitable donor cells. Suitable donor cells, i.e., cells useful in the subject invention, may be obtained from any cell or organ of the body. This includes all somatic or germ cells.

Fibroblast cells are an ideal cell type because they can be obtained from developing fetuses and adult animals in large quantities. Fibroblast cells are differentiated somewhat and, thus, were previously considered a poor cell type to use in cloning procedures. Importantly, these cells can be easily propagated in vitro with a rapid doubling time and can be clonally propagated for use in gene targeting procedures. Again the present invention is novel because differentiated cell types are used. The present invention is advantageous because the cells can be easily propagated, genetically modified and selected in vitro.

Suitable mammalian sources for oocytes include sheep, cows, pigs, horses, rabbits, guinea pigs, mice, hamsters, rats, primates, etc. Preferably, the oocytes will be obtained from ungulates, and most preferably bovine.

Methods for isolation of oocytes are well known in the art. Essentially, this will comprise isolating oocytes from the ovaries or reproductive tract of a mammal, e.g., a bovine. A readily available source of bovine oocytes is slaughterhouse materials.

For the successful use of techniques such as genetic engineering, nuclear transfer and cloning, oocytes must generally be matured in vitro before these cells may be used as recipient cells for nuclear transfer, and before they can be fertilized by the sperm cell to develop into an embryo. This process generally requires collecting immature (prophase I) oocytes from mammalian ovaries, e.g., bovine ovaries obtained at a slaughterhouse, and maturing the oocytes in a maturation medium prior to fertilization or enucleation until the oocyte attains the metaphase II stage, which in the case of bovine oocytes generally occurs about 18–24 hours post-aspiration. For purposes of the present invention, this period of time is known as the "maturation period." As used herein for calculation of time periods, "aspiration" refers to aspiration of the immature oocyte from ovarian follicles.

Additionally, metaphase II stage oocytes, which have been matured in vivo have been successfully used in nuclear transfer techniques. Essentially, mature metaphase II oocytes are collected surgically from either non-superovulated or superovulated cows or heifers 35 to 48 hours past the onset of estrus or past the injection of human chorionic gonadotropin (hCG) or similar hormone.

The stage of maturation of the oocyte at enucleation and nuclear transfer has been reported to be significant to the success of NT methods. (See e.g., Prather et al., *Differentiation*, 48, 1–8, 1991). In general, successful mammalian embryo cloning practices use the metaphase II stage oocyte as the recipient oocyte because at this stage it is believed that the oocyte can be or is sufficiently "activated" to treat the introduced nucleus as it does a fertilizing sperm. In domestic animals, and especially cattle, the oocyte activation period generally ranges from about 16–52 hours, preferably about 28–42 hours post-aspiration.

For example, immature oocytes may be washed in HEPES buffered hamster embryo culture medium (HECM) as described in Seshagine et al., *Biol. Reprod.*, 40, 544–606, 1989, and then placed into drops of maturation medium consisting of 50 microliters of tissue culture medium (TCM) 199 containing 10% fetal calf serum which contains appropriate gonadotropins such as luteinizing hormone (LH) and follicle stimulating hormone (FSH), and estradiol under a layer of lightweight paraffin or silicon at 39° C.

After a fixed time maturation period, which ranges from about 10 to 40 hours, and preferably about 16–18 hours, the oocytes will be enucleated. Prior to enucleation the oocytes will preferably be removed and placed in HECM containing 1 milligram per milliliter of hyaluronidase prior to removal of cumulus cells. This may be effected by repeated pipetting through very fine bore pipettes or by vortexing briefly. The stripped oocytes are then screened for polar bodies, and the selected metaphase II oocytes, as determined by the presence of polar bodies, are then used for nuclear transfer. Enucleation follows.

Enucleation may be effected by known methods, such as described in U.S. Pat. No. 4,994,384 which is incorporated by reference herein. For example, metaphase II oocytes are either placed in HECM, optionally containing 7.5 micrograms per milliliter cytochalasin B, for immediate enucleation, or may be placed in a suitable medium, for example an embryo culture medium such as CR1aa, plus 10% estrus cow serum, and then enucleated later, preferably not more than 24 hours later, and more preferably 16–18 hours later.

Enucleation may be accomplished microsurgically using a micropipette to remove the polar body and the adjacent cytoplasm. The oocytes may then be screened to identify those of which have been successfully enucleated. This screening may be effected by staining the oocytes with 1 microgram per milliliter 33342 Hoechst dye in HECM, and then viewing the oocytes under ultraviolet irradiation for less than 10 seconds. The oocytes that have been successfully enucleated can then be placed in a suitable culture medium, e.g., CR1aa plus 10% serum.

In the present invention, the recipient oocytes will preferably be enucleated at a time ranging from about 10 hours to about 40 hours after the initiation of in vitro maturation, more preferably from about 16 hours to about 24 hours after initiation of in vitro maturation, and most preferably about 16–18 hours after initiation of in vitro maturation.

A single mammalian cell of the same species as the enucleated oocyte will then be transferred into the perivitelline space of the enucleated oocyte used to produce the NT unit. The mammalian cell and the enucleated oocyte will be used to produce NT units according to methods known in the art. For example, the cells may be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels will open between the two cells. Due to the thermodynamic instability of such a small opening, it enlarges until the two cells become one. Reference is made to U.S. Pat. No. 4,997,384 by Prather et al., (incorporated by reference in its entirety herein) for a further discussion of this process. A variety of electrofusion media can be used including e.g., sucrose, mannitol, sorbitol and phosphate buffered solution. Fusion can also be accomplished using Sendai virus as a fusogenic agent (Graham, *Wister Inot. Symp. Monogr.*, 9, 19, 1969).

Also, in some cases (e.g. with small donor nuclei) it may be preferable to inject the nucleus directly into the oocyte rather than using electroporation fusion. Such techniques are disclosed in Collas and Barnes, *Mol. Reprod. Dev.*, 38:264–267 (1994), incorporated by reference in its entirety herein.

Preferably, the mammalian cell and oocyte are electrofused in a 500 μm chamber by application of an electrical pulse of 90–120 V for about 15 μsec, about 24 hours after initiation of oocyte maturation. After fusion, the resultant fused NT units are then placed in a suitable medium until activation, e.g., CR1aa medium. Typically activation will be effected shortly thereafter, typically less than 24 hours later, and preferably about 4–9 hours later.

The NT unit may be activated by known methods. Such methods include, e.g., culturing the NT unit at subphysiological temperature, in essence by applying a cold, or actually cool temperature shock to the NT unit. This may be most conveniently done by culturing the NT unit at room temperature, which is cold relative to the physiological temperature conditions to which embryos are normally exposed.

Alternatively, activation may be achieved by application of known activation agents. For example, penetration of oocytes by sperm during fertilization has been shown to activate prefusion oocytes to yield greater numbers of viable pregnancies and multiple genetically identical calves after nuclear transfer. Also, treatments such as electrical and chemical shock may be used to activate NT embryos after fusion. Suitable oocyte activation methods are the subject of U.S. Pat. No. 5,496,720, to Susko-Parrish et al., herein incorporated by reference in its entirety.

Additionally, activation may be effected by simultaneously or sequentially:

(i) increasing levels of divalent cations in the oocyte, and (ii) reducing phosphorylation of cellular proteins in the oocyte.

This will generally be effected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators.

Phosphorylation may be reduced by known methods, e.g., by the addition of kinase inhibitors, e.g., serine-threonine kinase inhibitors, such as 6-dimethyl-aminopurine, staurosporine, 2-aminopurine, and sphingosine.

Alternatively, phosphorylation of cellular proteins may be inhibited by introduction of a phosphatase into the oocyte, e.g., phosphatase 2A and phosphatase 2B.

In one embodiment, NT activation is effected by briefly exposing the fused NT unit to a TL-HEPES medium containing 5 μM ionomycin and 1 mg/ml BSA, followed by washing in TL-HEPES containing 30 mg/ml BSA within about 24 hours after fusion, and preferably about 4 to 9 hours after fusion.

The activated NT units may then be cultured in a suitable in vitro culture medium until the generation of CICM cells and cell colonies. Culture media suitable for culturing and maturation of embryos are well known in the art. Examples of known media, which may be used for bovine embryo culture and maintenance, include Ham's F-10+10% fetal calf serum (FCS), Tissue Culture Medium-199 (TCM-199)+ 10% fetal calf serum, Tyrodes-Albumin-Lactate-Pyruvate (TALP), Dulbecco's Phosphate Buffered Saline (PBS), Eagle's and Whitten's media. One of the most common media used for the collection and maturation of oocytes is TCM-199, and 1 to 20% serum supplement including fetal calf serum, newborn serum, estrual cow serum, lamb serum or steer serum. A preferred maintenance medium includes TCM-199 with Earl salts, 10% fetal calf serum, 0.2 mM Na pyruvate and 50 μg/ml gentamicin sulphate. Any of the above may also involve co-culture with a variety of cell types such as granulosa cells, oviduct cells, BRL cells and uterine cells and STO cells.

Another maintenance medium is described in U.S. Pat. No. 5,096,822 to Rosenkrans, Jr. et al., which is incorporated herein by reference. This embryo medium, named CR1, contains the nutritional substances necessary to support an embryo.

CR1 contains hemicalcium L-lactate in amounts ranging from 1.0 mM to 10 mM, preferably 1.0 mM to 5.0 mM. Hemicalcium L-lactate is L-lactate with a hemicalcium salt incorporated thereon. Hemicalcium L-lactate is significant in that a single component satisfies two major requirements in the culture medium: (i) the calcium requirement necessary for compaction and cytoskeleton arrangement; and (ii) the lactate requirement necessary for metabolism and electron transport. Hemicalcium L-lactate also serves as valuable mineral and energy source for the medium necessary for viability of the embryos.

Advantageously, CR1 medium does not contain serum, such as fetal calf serum, and does not require the use of a co-culture of animal cells or other biological media, i.e., media comprising animal cells such as oviductal cells. Biological media can sometimes be disadvantageous in that they may contain microorganisms or trace factors which may be harmful to the embryos and which are difficult to detect, characterize and eliminate.

Examples of the main components in CR1 medium include hemicalcium L-lactate, sodium chloride, potassium chloride, sodium bicarbonate and a minor amount of fatty-acid free bovine serum albumin (Sigma A-6003). Additionally, a defined quantity of essential and non-essential amino acids may be added to the medium. CR1 with amino acids is known by the abbreviation "CR1aa."

CR1 medium preferably contains the following components in the following quantities:

| | |
|---|---|
| sodium chloride | - 114.7 mM |
| potassium chloride | - 3.1 mM |
| sodium bicarbonate | - 26.2 mM |
| hemicalcium L-lactate | - 5 mM |
| fatty-acid free BSA | - 3 mg/ml |

In one embodiment, the activated NT embryos unit are placed in CR1aa medium containing 1.9 mM DMAP for about 4 hours followed by a wash in HECM and then cultured in CR1aa containing BSA.

For example, the activated NT units may be transferred to CR1aa culture medium containing 2.0 mM DMAP (Sigma) and cultured under ambient conditions, e.g., about 38.5° C., 5% $CO_2$ for a suitable time, e.g., about 4 to 5 hours.

Afterward, the cultured NT unit or units are preferably washed and then placed in a suitable media, e.g., CR1aa medium containing 10% FCS and 6 mg/ml contained in well plates which preferably contain a suitable confluent feeder layer. Suitable feeder layers include, by way of example, fibroblasts and epithelial cells, e.g., fibroblasts and uterine epithelial cells derived from ungulates, chicken fibroblasts, murine (e.g., mouse or rat) fibroblasts, STO and SI-m220 feeder cell lines, and BRL cells.

In one embodiment, the feeder cells comprise mouse embryonic fibroblasts. Preparation of a suitable fibroblast feeder layer is described in the example which follows and is well within the skill of the ordinary artisan.

The NT units are cultured on the feeder layer until the NT units reach a size suitable for transferring to a recipient female, or for obtaining cells which may be used to produce CICM cells or cell colonies. Preferably, these NT units will be cultured until at least about 2 to 400 cells, more preferably about 4 to 128 cells, and most preferably at least about 50 cells. The culturing will be effected under suitable conditions, i.e., about 38.5° C. and 5% $CO_2$, with the culture medium changed in order to optimize growth typically about every 2–5 days, preferably about every 3 days.

The methods for embryo transfer and recipient animal management in the present invention are standard procedures used in the embryo transfer industry. Synchronous transfers are important for success of the present invention, i.e., the stage of the NT embryo is in synchrony with the estrus cycle of the recipient female. This advantage and how to maintain recipients are reviewed in Siedel, G. E., Jr. ("Critical review of embryo transfer procedures with cattle" in *Fertilization and Embryonic Development in Vitro* (1981) L. Mastroianni, Jr. and J. D. Biggers, ed., Plenum Press, New York, N.Y., page 323), the contents of which are hereby incorporated by reference.

The present invention can also be used to clone genetically engineered or transgenic mammals. As explained above, the present invention is advantageous in that transgenic procedures can be simplified by working with a differentiated cell source that can be clonally propagated. In particular, the differentiated cells used for donor nuclei have a desired gene inserted, removed or modified. Those genetically altered, differentiated cells are then used for nuclear transplantation with enucleated oocytes.

Any known method for inserting, deleting or modifying a desired gene from a mammalian cell may be used for altering the differentiated cell to be used as the nuclear donor. These procedures may remove all or part of a gene, and the gene may be heterologous. Included is the technique of homologous recombination, which allows the insertion, deletion or modification of a gene or genes at a specific site or sites in the cell genome.

The present invention can thus be used to provide adult mammals with desired genotypes. Multiplication of adult ungulates with proven genetic superiority or other desirable traits is particularly useful, including transgenic or genetically engineered animals, and chimeric animals. Furthermore, cell and tissues from the NT fetus, including transgenic and/or chimeric fetuses, can be used in cell, tissue and organ transplantation for the treatment of numerous diseases as described below in connection with the use of CICM cells.

For production of CICM cells and cell lines, after NT units of the desired size are obtained, the cells are mechanically removed from the zone and are then used. This is preferably effected by taking the clump of cells which comprise the NT unit, which typically will contain at least about 50 cells, washing such cells, and plating the cells onto a feeder layer, e.g., irradiated fibroblast cells. Typically, the cells used to obtain the stem cells or cell colonies will be obtained from the inner most portion of the cultured NT unit which is preferably at least 50 cells in size. However, NT units of smaller or greater cell numbers as well as cells from other portions of the NT unit may also be used to obtain ES cells and cell colonies. The cells are maintained in the feeder layer in a suitable growth medium, e.g., alpha MEM supplemented with 10% FCS and 0.1 mM β-mercaptoethanol (Sigma) and L-glutamine. The growth medium is changed as often as necessary to optimize growth, e.g., about every 2–3 days.

This culturing process results in the formation of CICM cells or cell lines. One skilled in the art can vary the culturing conditions as desired to optimize growth of the particular CICM cells. Also, genetically engineered or transgenic mammalian CICM cells may be produced according to the present invention. That is, the methods described above can be used to produce NT units in which a desired gene or genes have been introduced, or from which all or part of an endogenous gene or genes have been removed or modified. Those genetically engineered or transgenic NT units can then be used to produce genetically engineered or transgenic CICM cells, including human cells.

The resultant CICM cells and cell lines, preferably human CICM cells and cell lines, have numerous therapeutic and diagnostic applications. Most especially, such CICM cells may be used for cell transplantation therapies. Human CICM cells have application in the treatment of numerous disease conditions. Human NT units per se may also be used in the treatment of disease conditions.

In this regard, it is known that mouse embryonic stem (ES) cells are capable of differentiating into almost any cell type, e.g., hematopoietic stem cells. Therefore, human CICM cells produced according to the invention should possess similar differentiation capacity. The CICM cells according to the invention will be induced to differentiate to obtain the desired cell types according to known methods. For example, the subject human CICM cells may be induced to differentiate into hematopoietic stem cells, muscle cells, cardiac muscle cells, liver cells, cartilage cells, epithelial cells, urinary tract cells, etc., by culturing such cells in differentiation medium and under conditions which provide for cell differentiation. Medium and methods which result in the differentiation of CICM cells are known in the art as are suitable culturing conditions.

For example, Palacios et al, *Proc. Natl. Acad. Sci., USA*, 92:7530–7537 (1995) teaches the production of hematopoietic stem cells from an embryonic cell line by subjecting stem cells to an induction procedure comprising initially culturing aggregates of such cells in a suspension culture medium lacking retinoic acid followed by culturing in the same medium containing retinoic acid, followed by transferral of cell aggregates to a substrate which provides for cell attachment.

Moreover, Pedersen, *J. Reprod. Fertil. Dev.*, 6:543–552 (1994) is a review article which references numerous articles disclosing methods for in vitro differentiation of embryonic stem cells to produce various differentiated cell types including hematopoietic cells, muscle, cardiac muscle, nerve cells, among others.

Further, Bain et al, *Dev. Biol.*, 168:342–357 (1995) teaches in vitro differentiation of embryonic stem cells to produce neural cells which possess neuronal properties. These references are exemplary of reported methods for obtaining differentiated cells from embryonic or stem cells. These references and in particular the disclosures therein relating to methods for differentiating embryonic stem cells are incorporated by reference in their entirety herein.

Thus, using known methods and culture medium, one skilled in the art may culture the subject CICM cells, including genetically engineered or transgenic CICM cells, to obtain desired differentiated cell types, e.g., neural cells, muscle cells, hematopoietic cells, etc.

The subject CICM cells may be used to obtain any desired differentiated cell type. Therapeutic usages of such differentiated human cells are unparalleled. For example, human hematopoietic stem cells may be used in medical treatments requiring bone marrow transplantation. Such procedures are used to treat many diseases, e.g., late stage cancers such as ovarian cancer and leukemia, as well as diseases that compromise the immune system, such as AIDS. Hematopoietic stem cells can be obtained, e.g., by fusing adult somatic cells of a cancer or AIDS patient, e.g., epithelial cells or lymphocytes with an enucleated oocyte, obtaining CICM cells as described above, and culturing such cells under conditions which favor differentiation, until hematopoietic stem cells are obtained. Such hematopoietic cells may be used in the treatment of diseases including cancer and AIDS.

Alternatively, adult somatic cells from a patient with a neurological disorder may be fused with an enucleated oocyte, human CICM cells obtained therefrom, and such cells cultured under differentiation conditions to produce neural cell lines. Specific diseases treatable by transplantation of such human neural cells include, by way of example, Parkinson's disease, Alzheimer's disease, ALS and cerebral palsy, among others. In the specific case of Parkinson's disease, it has been demonstrated that transplanted fetal brain neural cells make the proper connections with surrounding cells and produce dopamine. This can result in long-term reversal of Parkinson's disease symptoms.

The great advantage of the subject invention is that it provides an essentially limitless supply of isogenic or syngenic human cells suitable for transplantation. Therefore, it will obviate the significant problem associated with current transplantation methods, i.e., rejection of the transplanted tissue which may occur because of host-vs-graft or graft-vs-host rejection. Conventionally, rejection is prevented or reduced by the administration of anti-rejection drugs such as cyclosporine. However, such drugs have significant adverse side-effects, e.g., immunosuppression, carcinogenic properties, as well as being very expensive. The present invention should eliminate, or at least greatly reduce, the need for anti-rejection drugs.

Other diseases and conditions treatable by isogenic cell therapy include, by way of example, spinal cord injuries, multiple sclerosis, muscular dystrophy, diabetes, liver diseases, i.e., hypercholesterolemia, heart diseases, cartilage replacement, burns, foot ulcers, gastrointestinal diseases, vascular diseases, kidney disease, urinary tract disease, and aging related diseases and conditions.

This methodology can be used to replace defective genes, e.g., defective immune system genes, cystic fibrosis genes, or to introduce genes which result in the expression of therapeutically beneficial proteins such as growth factors, lymphokines, cytokines, enzymes, etc. For example, the gene encoding brain derived growth factor may be introduced into human CICM cells, the cells differentiated into neural cells and the cells transplanted into a Parkinson's patient to retard the loss of neural cells during such disease.

Previously, cell types transfected with BDNF varied from primary cells to immortalized cell lines, either neural or non-neural (myoblast and fibroblast) derived cells. For example, astrocytes have been transfected with BDNF gene using retroviral vectors, and the cells grafted into a rat model of Parkinson's disease (Yoshimoto et al., *Brain Research*, 691:25–36, (1995)).

This ex vivo therapy reduced Parkinson's-like symptoms in the rats up to 45% 32 days after transfer. Also, the tyrosine hydroxylase gene has been placed into astrocytes with similar results (Lundberg et al., *Develop. Neurol.*, 139:39–53 (1996) and references cited therein).

However, such ex vivo systems have problems. In particular, retroviral vectors currently used are downregulated in vivo and the transgene is only transiently expressed (review by Mulligan, *Science*, 260:926–932 (1993)). Also, such studies used primary cells, astrocytes, which have finite life span and replicate slowly. Such properties adversely affect the rate of transfection and impede selection of stably transfected cells. Moreover, it is almost impossible to propagate a large population of gene targeted primary cells to be used in homologous recombination techniques. By contrast, the difficulties associated with retroviral systems should be eliminated by the use of mammalian CICM cells.

Genes which may be introduced into the subject CICM cells include, by way of example, epidermal growth factor, basic fibroblast growth factor, glial derived neurotrophic growth factor, insulin-like growth factor (I and II), neurotrophin-3, neurotrophin-4/5, ciliary neurotrophic factor, AFT-1, cytokine genes (interleukins, interferons, colony stimulating factors, tumor necrosis factors (alpha and beta), etc.), genes encoding therapeutic enzymes, etc.

In addition to the use of human CICM cells in cell, tissue and organ transplantation, the present invention also includes the use of non-human cells in the treatment of human diseases. Thus, CICM cells, NT fetuses and NT and chimeric offspring (transgenic or non-transgenic) of any species may be used in the treatment of human disease conditions where cell, tissue or organ transplantation is warranted. In general, CICM cell, fetuses and offspring according to the present invention can be used within the same species (autologous, syngenic or allografts) or across species (xenografts). For example, brain cells from bovine NT fetuses may be used to treat Parkinson's disease.

Also, the subject CICM cells, preferably human cells, may be used as an in vitro model of differentiation, in particular for the study of genes which are involved in the regulation of early development. Also, differentiated cell tissues and organs using the subject CICM cells may be used in drug studies.

Further, the subject CICM cells may be used as nuclear donors for the production of other CICM cells and cell colonies.

In order to more clearly describe the subject invention, the following examples are provided.

EXAMPLE 1

Isolation of Primary Cultures of Bovine and Porcine Embryonic and Adult Bovine Fibroblast Cells Primary cultures of bovine and porcine fibroblasts were obtained from fetuses (45 days of pregnancy for cattle and 35 days for pig fetuses). The head, liver, heart and alimentary tract were aseptically removed, the fetuses minced and incubated for 30 minutes at 37° C. in prewarmed trypsin EDTA solution (0.05% trypsin/0.02% EDTA; GIBCO, Grand Island, N.Y.). Fibroblast cells were plated in tissue culture dishes and cultured in alpha-MEM, medium (BioWhittaker, Walkersville, Md.) supplemented with 10% fetal calf serum (FCS) (Hyclone, Logen, Utah), penicillin (100 IU/ml) and streptomycin (50 μl/ml). The fibroblasts were grown and maintained in a humidified atmosphere with 5% $CO_2$ in air at 37° C.

Adult fibroblast cells were isolated from the lung of a cow (approximately five years of age). Minced lung tissue was incubated overnight at 10° C. in trypsin EDTA solution (0.05% trypsin/0.02% EDTA; GIBCO, Grand Island, N.Y.). The following day tissue and any disassociated cells were incubated for one hour at 37° C. in prewarmed trypsin EDTA solution (0.05% trypsin/0.02% EDTA; GIBCO, Grand Island, N.Y.) and processed through three consecutive washes and trypsin incubations (one hr). Fibroblast cells were plated in tissue culture dishes and cultured in alpha-MEM medium (BioWhittaker, Walkersville, Md.) supplemented with 10% fetal calf serum (FCS) (Hyclone, Logen, Utah), penicillin (100 IU/ml) and streptomycin (50 μl/ml). The fibroblast cells can be isolated at virtually any time in development, ranging from approximately post embryonic disc stage through adult life of the animal (bovine day 12 to 15 after fertilization to 10 to 15 years of age animals). This procedure can also be used to isolate fibroblasts from other mammals, including mice.

Introduction of a Marker Gene (foreign heterologous DNA) into Embryonic and Adult Fibroblast Cells The following electroporation procedure was conducted for both embryonic (cattle and pigs) and adult (cattle) fibroblast cells. Standard microinjection procedures may also be used to introduce heterologous DNA into fibroblast cells, however, in this example electroporation was used because it is an easier procedure.

Culture plates containing propagating fibroblast cells were incubated in trypsin EDTA solution (0.05% trypsin/0.02% EDTA; GIBCO, Grand Island, N.Y.) until the cells were in a single cell suspension. The cells were spun down at 500×g and re-suspended at 5 million cells per ml with phosphate buffered saline (PBS).

The reporter gene construct contained the cytomegalovirus promoter and the beta-galactosidase, neomycin phosphotransferase fusion gene (beta-GEO). The reporter gene and the cells at 50 μg/ml final concentration were added to the electroporation chamber. After the electroporation pulse, the fibroblast cells were transferred back into the growth medium (alpha-MEM medium (BioWhittaker, Walkersville, Md.) supplemented with 10% fetal calf serum (FCS) (Hyclone, Logen, Utah), penicillin (100 IU/ml) and streptomycin (50 μl/ml)).

The day after electroporation, attached fibroblast cells were selected for stable integration of the reporter gene. G418 (400 μg/ml) was added to growth medium for 15 days (range: 3 days until the end of the cultured cells' life span). This drug kills any cells without the beta-GEO gene, since they do not express the neo resistance gene. At the end of this time, colonies of stable transgenic cells were present. Each colony was propagated independently of each other. Transgenic fibroblast cells were stained with X-gal to observe expression of beta-galactosidase, and confirmed positive for integration using PCR amplification of the beta-GEO gene and run out on an agarose gel.

Use of Transgenic Fibroblast Cells in Nuclear Transfer Procedures to Create CICM Cell Lines and Transgenic Fetuses One line of cells (CL-1) derived from one colony of bovine embryonic fibroblast cells was used as donor nuclei in the nuclear transfer (NT) procedure. General NT procedures are described above.

Slaughterhouse oocytes were matured in vitro. The oocytes were stripped of cumulus cells and enucleated with a beveled micropipette at approximately 18 to 20 hrs post maturation (hpm). Enucleation was confirmed in TL-HEPES medium plus Hoechst 33342 (3 μg/ml; Sigma). Individual donor cells (fibroblasts) were then placed in the perivitelline space of the recipient oocyte. The bovine oocyte cytoplasm and the donor nucleus (NT unit) were fused together using electrofusion techniques. One fusion pulse consisting of 120 V for 15 μsec in a 500 μm gap chamber was applied to the NT unit. This occurred at 24 hpm. The NT units were placed in CR1aa medium until 26 to 27 hpm.

The general procedure used to artificially activate oocytes has been described above. NT unit activation was initiated between 26 and 27 hpm. Briefly, NT units were exposed for four min to ionomycin (5 μM; CalBiochem, La Jolla, Calif.) in TL-HEPES supplemented with 1 mg/ml BSA and then washed for five min in TL-HEPES supplemented with 30 mg/ml BSA. Throughout the ionomycin treatment, NT units were also exposed to 2 mM DMAP (Sigma). Following the wash, NT units were then transferred into a microdrop of CR1aa culture medium containing 2 mM DMAP (Sigma) and cultured at 38.5° C. 5% $CO_2$ for four to five hrs. The embryos were washed and then placed in CR1aa medium plus 10% FCS and 6 mg/ml BSA in four well plates containing a confluent feeder layer of mouse embryonic fibroblast. The NT units were cultured for three more days at 38.5° C. and 5% $CO_2$. Culture medium was changed every three days until days 5 to 8 after activation. At this time blastocyst stage NT embryos can be used to produce transgenic CICM (cultured inner cell mass) cell lines or fetuses. The inner cell mass of these NT units can be isolated and plated on a feeder layer. Also, NT units were transferred into recipient females. The pregnancies were aborted at 35 days of gestation. This resulted in two cloned transgenic fetuses having the beta-GEO gene in all tissues checked. Thus, this is a fast and easy method of making transgenic CICM cell lines and fetuses. This procedure is generally conducive to gene targeted CICM cell lines and fetuses.

The table below summarizes the results of these 15 experiments.

| donor cell type | n | cleavage (%) | blasto-cysts (%) | CICM* lines (%) | transgenic fetuses (%) |
|---|---|---|---|---|---|
| CL-1 bovine embyonic fibroblasts (bGEO) | 412 | 220 (53) | 40 (10%) | 22 (55%) | |
| CL-1 bovine embryonic fibroblast (bGEO) | 505 | | 46 (9%) | | 4 fetuses †/16 embryos (20%) |
| CICM cell line derived from CL-1 NT embryos | 709 | | 5 (0.7%) | | |

*19 lines were positive for beta-GEO, 2 were negative and one line died prior to PCR detection.
†One fetus was dead and another was slightly retarded in development at 35 days of gestation. Two fetuses recovered at day 38 were normal. All fetuses were confirmed transgenic.

EXAMPLE 2

Chimeric Fetuses Derived from Transgenic CICM Cells. The Transgenic CICM Cell Line was Derived Originally from a Transgenic NT Unit (differentiated cell).

A CICM line derived from transgenic NT embryos (a CL-1 cell transferred into an enucleated oocyte) was used to produce chimeric embryos and fetuses. Colonies of transgenic CICM cells were disaggregated either using 1–5 mg/ml pronase or 0.05% trypsin/EDTA combined with mechanical disaggregation methods so that clumps of five or fewer cells were produced. Trypsin or pronase activity was inactivated by passing the cells through multiple washes of 30 to 100% fetal calf serum. The disaggregated cells were placed in micromanipulation plates containing TL-HEPES medium. Fertilized embryos were also placed in these plates and micromanipulation tools were used to produce the chimeric embryos. Eight to ten transgenic CICM cells were injected into 8–16 cell stage fertilized embryos. These embryos were cultured in vitro to the blastocyst stage and then transferred into recipient animals.

A total of 6 blastocyst stage chimeric embryos were non-surgically transferred into two recipient females. After five weeks of gestation 3 fetuses were recovered. Several tissues of the three fetuses, including germ cells of the gonad (suggesting germ-line chimeras), were screened by PCR amplification and southern blot hybridization of the amplified product to a beta-galactosidase fragment. Of the three fetuses, two were positive for contribution from the transgenic CICM cells. Both of these fetuses had transgenic CICM contribution to the gonad.

Transgenic NT Embryos Derived from Transgenic CICM Cell Lines. The Transgenic CICM Cell Line was Derived Originally from a Transgenic NT Unit (differentiated cell).

The same transgenic CICM cell lines were used to produce NT embryos. The NT procedures described in Example 1 were used except that CICM cells instead of fibroblast cells were used as the donor cell fused with the enucleated oocyte. Colonies of transgenic CICM cells were disaggregated either using 1–5 mg/ml pronase or 0.05% trypsin/EDTA combined with mechanical disaggregation methods so that clumps of five or fewer cells were produced. Trypsin or pronase activity was inactivated by passing the cells through multiple washes of 30 to 100% fetal calf serum before transferring the cells into enucleated oocytes. Results are reported in Table 1 (third group). Five blastocyst stage embryos were produced.

What is claimed is:

1. An improved method of cloning a non-human mammal by nuclear transfer comprising the introduction of a non-human mammalian donor cell or a non-human mammalian donor cell nucleus into a non-human mammalian enucleated oocyte of the same species as the donor cell or donor cell nucleus to form a nuclear transfer (NT) unit, implantation of the NT unit into the uterus of a surrogate mother of said species, and permitting the NT unit to develop into the cloned mammal, wherein the improvement comprises using as the donor cell or donor cell nucleus a proliferating somatic cell that has been expanded in culture, or a nucleus isolated from said somatic cell.

2. An improved method of cloning a non-human mammal by nuclear transfer comprising the introduction of a non-human mammalian donor cell or a non-human mammalian donor cell nucleus into a non-human mammalian enucleated oocyte of the same species as the donor cell or donor cell nucleus to form a nuclear transfer (NT) unit, implantation of the NT unit into the uterus of a surrogate mother of said species, and permitting the NT unit to develop into the cloned mammal, wherein the improvement comprises using as the donor cell or donor cell nucleus a proliferating somatic cell that has been expanded in culture, or a nucleus isolated from said somatic cell, and wherein the donor cell or donor cell nucleus has been genetically transformed to comprise at least one addition, substitution or deletion of a nucleic acid sequence.

3. A method of cloning a non-human mammal by nuclear transfer comprising the following steps:
   (i) inserting a desired non-human mammalian proliferating somatic cell that has been expanded in culture, or a nucleus isolated from said somatic cell, into a non-human mammalian enucleated oocyte of the same species under conditions suitable for the formation of a nuclear transfer (NT) unit;

(ii) activating the resultant nuclear transfer unit;

(iii) culturing said activated NT unit until greater than the 2-cell developmental stage; and (iv) transferring said cultured NT unit to a host non-human mammal of the same species such that the NT develops in to a non-human mammal.

4. An improved method of cloning a non-human mammalian fetus by nuclear transfer comprising the introduction of a non-human mammalian donor cell or a non-human mammalian donor cell nucleus into a non-human mammalian enucleated oocyte of the same species as the donor cell or donor cell nucleus to form a nuclear transfer (NT) unit, implantation of the NT unit into the uterus of a surrogate mother of the same species, and permitting the NT unit to develop into the mammalian fetus, wherein the improvement comprises using as the donor cell or donor cell nucleus a proliferating somatic cell that has been expanded in culture, or a nucleus isolated from said somatic cell.

5. An improved method of cloning a non-human mammalian fetus by nuclear transfer comprising the introduction of a non-human mammalian donor cell or a non-human mammalian donor cell nucleus into a non-human mammalian enucleated oocyte of the same species as the donor cell or donor cell nucleus to form a nuclear transfer (NT) unit, implantation of the NT unit into the uterus of a surrogate mother of the same species, and permitting the NT unit to develop into the mammalian fetus, wherein the improvement comprises using as the donor cell or donor cell nucleus a proliferating somatic cell that has been expanded in culture, or a nucleus isolated from said somatic cell, and wherein the donor cell or donor cell nucleus has been genetically transformed to comprises at least one addition, substitution or deletion of a nucleic acid sequence.

6. A method of cloning a non-human mammalian fetus by nuclear transfer comprising the following steps:

(i) inserting a desired non-human mammalian proliferating somatic cell that has been expanded in culture, or a nucleus isolated from said somatic cell, into a non-human mammalian enucleated oocyte of the same species under conditions suitable for the formation of a nuclear transfer (NT) unit;

(ii) activating the resultant nuclear transfer unit;

(iii) culturing said activated NT unit until greater than the 2-cell developmental stage; and (iv) transferring said cultured NT unit to a host non-human mammal of the same species such that the NT develops into a fetus.

7. The method of any of claims 4–6, wherein the fetus develops into an offspring.

8. The method of any of claims 1–6, wherein the donor cell or donor cell nucleus is from mesoderm.

9. The method of any of claims 1–6, wherein the donor cell or donor cell nucleus is from endoderm.

10. The method of any of claims 1–6, wherein the donor cell or donor cell nucleus is from ectoderm.

11. The method of any of claims 1–6, wherein the donor cell or donor cell nucleus is from a fibroblast.

12. The method of any of claims 1–6, wherein the donor cell or donor cell nucleus is from an ungulate.

13. The method of any of claims 1–6, wherein the donor cell or donor cell nucleus is from an ungulate selected from the group consisting of bovine, ovine, porcine, equine, caprine and buffalo.

14. The method of any of claims 1–6, wherein the donor cell or donor cell nucleus is from a non-human mammalian fetus.

15. The method of any of claims 1–6, wherein the donor cell or donor cell nucleus is from an adult non-human mammalian cell.

16. The method of any of claims 1–6, wherein the donor cell or donor cell nucleus is selected from the group consisting of epithelial cells, neural cells, epidermal cells, keratinocytes, hematopoietic cells, melanocytes, chondrocytes, B-lymphocytes, T-lymphocytes, erythrocytes, macrophages, monocytes, fibroblasts, muscle cells, and nuclei isolated therefrom.

17. The method of any of claims 1–6, wherein the donor cell or donor cell nucleus is from an organ selected from the group consisting of skin, lung, pancreas, liver, stomach, intestine, heart, reproductive organ, bladder, kidney and urethra.

18. The method of any of claims 1–6, wherein the oocyte is matured in vitro or in vivo prior to enucleation.

19. The method of any of claims 1–6, wherein the oocyte is matured in vitro prior to enucleation.

20. The method of any of claims 1–6, wherein the oocyte is enucleated by micro-surgical methods.

21. The method of any of claims 1–6, wherein the oocyte is enucleated about 10 to 40 hours after initiation of in vitro maturation.

22. The method of any of claims 1–6, wherein the oocyte is matured in vivo prior to enucleation.

23. The method of any of claims 1–6, wherein the non-human mammal is bovine.

24. The method of any of claims 1–6, wherein the non-human mammal is bovine.

* * * * *

Adverse Decisions in Interference

Patent No. 5,945,577, Jose Cibelli, James Robl, Paul Golueke, F. Abel Ponce de Leon, and D. Joseph Jerry, CLONING USING DONOR NUCLEI FROM PROLIFERATING SOMATIC CELLS, Interference No. 104,746, final judgment adverse to the patentees rendered December 20, 2004, as to claims 1-24.
*(Official Gazette January 16, 2007)*